(12) United States Patent
Panarello

(10) Patent No.: US 11,323,452 B2
(45) Date of Patent: May 3, 2022

(54) HIEARCHICAL ACCESS GROUPS FOR CONTROLLING DATA ACCESS, ESPECIALLY PATIENT DATA ACCESS

(71) Applicant: International Business Machines Corporation, Armonk, NY (US)

(72) Inventor: Dominic James Panarello, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 657 days.

(21) Appl. No.: 16/257,409

(22) Filed: Jan. 25, 2019

(65) Prior Publication Data
US 2020/0244667 A1 Jul. 30, 2020

(51) Int. Cl.
| | | |
|---|---|---|
| *H04L 9/40* | (2022.01) | |
| *H04L 29/06* | (2006.01) | |
| *G06F 21/62* | (2013.01) | |
| *G06F 21/60* | (2013.01) | |
| *H04L 67/564* | (2022.01) | |
| *H04L 67/60* | (2022.01) | |

(Continued)

(52) U.S. Cl.
CPC .......... *H04L 63/104* (2013.01); *G06F 21/604* (2013.01); *G06F 21/6245* (2013.01); *G16H 10/60* (2018.01); *H04L 63/102* (2013.01); *H04L 67/1044* (2013.01); *H04L 67/2819* (2013.01); *H04L 67/32* (2013.01); *G06F 2221/2141* (2013.01)

(58) Field of Classification Search
CPC . H04L 63/104; H04L 63/102; H04L 67/2819; H04L 67/32; H04L 67/1044; H04L 67/1095; G06F 21/6245; G06F 21/604; G06F 2221/2141; G16H 10/60
See application file for complete search history.

(56) References Cited

U.S. PATENT DOCUMENTS

| | | | |
|---|---|---|---|
| 2005/0044409 A1* | 2/2005 | Betz ...................... | G06F 21/629 726/4 |
| 2006/0047725 A1* | 3/2006 | Bramson ............... | G06F 21/604 |

(Continued)

OTHER PUBLICATIONS

Wikipedia, "Group (computing)" downloaded on Jan. 14, 2019, https://en.wikipedia.org/wiki/Group_(computing) Jan. 14, 2019.
(Continued)

*Primary Examiner* — Khoi V Le
(74) *Attorney, Agent, or Firm* — Fleit Intellectual Property Law; Jon Gibbons

(57) ABSTRACT

A system and process for applying access groups for controlling data access, by a processor device. The process receives from a user a request to access data associated with a person from a file system, whereby the request invokes at least one software method. Next method interception is performed by matching the at least one software method. Group membership of the user and at least one group membership of the person is accessed. Determining if each of the following conditions of i) the user is a member of a specific group and ii) the specific group contains the person are verified. In response to the conditions being verified, the process sends the data to a user device to display to the user, otherwise denying the request to access data. Each group can have one or more criteria, which add patients to that group based on the conditions of those criteria.

21 Claims, 9 Drawing Sheets

(51) Int. Cl.
    *G16H 10/60*     (2018.01)
    *H04L 67/1042*     (2022.01)

(56) References Cited

U.S. PATENT DOCUMENTS

2007/0288759 A1* 12/2007 Wood .................. G06Q 20/341
                                                                                713/186
2018/0150650 A1*  5/2018 Saunders ............... G16H 10/60
2018/0247064 A1*  8/2018 Aronovich .......... G06F 21/6209

OTHER PUBLICATIONS

Motivation • google/guice Wiki • GitHub, downloaded on Jan. 14, 2019, https://github.com/google/guice/wiki/Motivation Apr. 20, 2015.

* cited by examiner

HIEARCHICAL ACCESS GROUPS FOR CONTROLLING DATA ACCESS, ESPECIALLY PATIENT DATA ACCESS

BACKGROUND

This invention generally relates to computer security and access control and, more specifically, to granting access to specific data after the user has been authenticated.

In computing, the term group generally refers to a grouping of users. In principle, users may belong to none, one, or many groups (although in practice, some systems place limits on this.) The primary purpose of user groups is to simplify access control to computer systems.

IBM Watson Care Manager (WCM) recently introduced a "data access" model that determines which users can access which patient's personal health information (PHI) through care team membership, registration, or emergency access.

It was determined that the current data access is too restrictive for use cases where users need access to a broad cohort of clients.

SUMMARY

Disclosed is a novel system and method to provide data access to a patient's PHI based on care team membership, dynamic data attributes e.g., patient condition, other groups, and more. For example, users, such as patient care managers, can receive access to patients through data access groups, of which a user may be a member. For example, a respiratory specialist can access all patients with a diagnosis of asthma. The set of patients in a group is based on rules which are defined by administrators. Users are also added to groups by administrators.

Further disclosed is a system and process for applying access groups for controlling data access, by a processor device. The process receives a request from a user to access data associated with a person from a file system, whereby the request invokes a software method. Next, method interception is performed by matching the software method. Group membership of the user and group membership of the person are accessed. Determining if each of the following two conditions of i) the user is a member of a specific group and ii) the specific group contains the person are both verified. In response to the two conditions are both verified, the process sends the data to a user device to display to the user, otherwise denying the request to access data.

Each group can have one or more criteria, which add patients to that group based on the conditions of those criteria. The criteria types can be mixed within the same group, e.g. multiple care team criteria alongside dynamic data criteria. Patients can also be explicitly included or excluded from a group. Patients can qualify for many groups. Users can be members of many groups.

The present invention includes intelligent caching. The intelligent caching includes storing in a software or hardware cache the criteria denoting the group membership, the group membership of the person, group membership of the user, the hierarchical structure of the group and any subgroups, and temporal data, which is clinical data, personal information data.

The foregoing and other features and advantages of the present invention will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention will be apparent from the following detailed description, taken in conjunction with the accompanying drawings in which:

DETAILED DESCRIPTION

Figure 1:
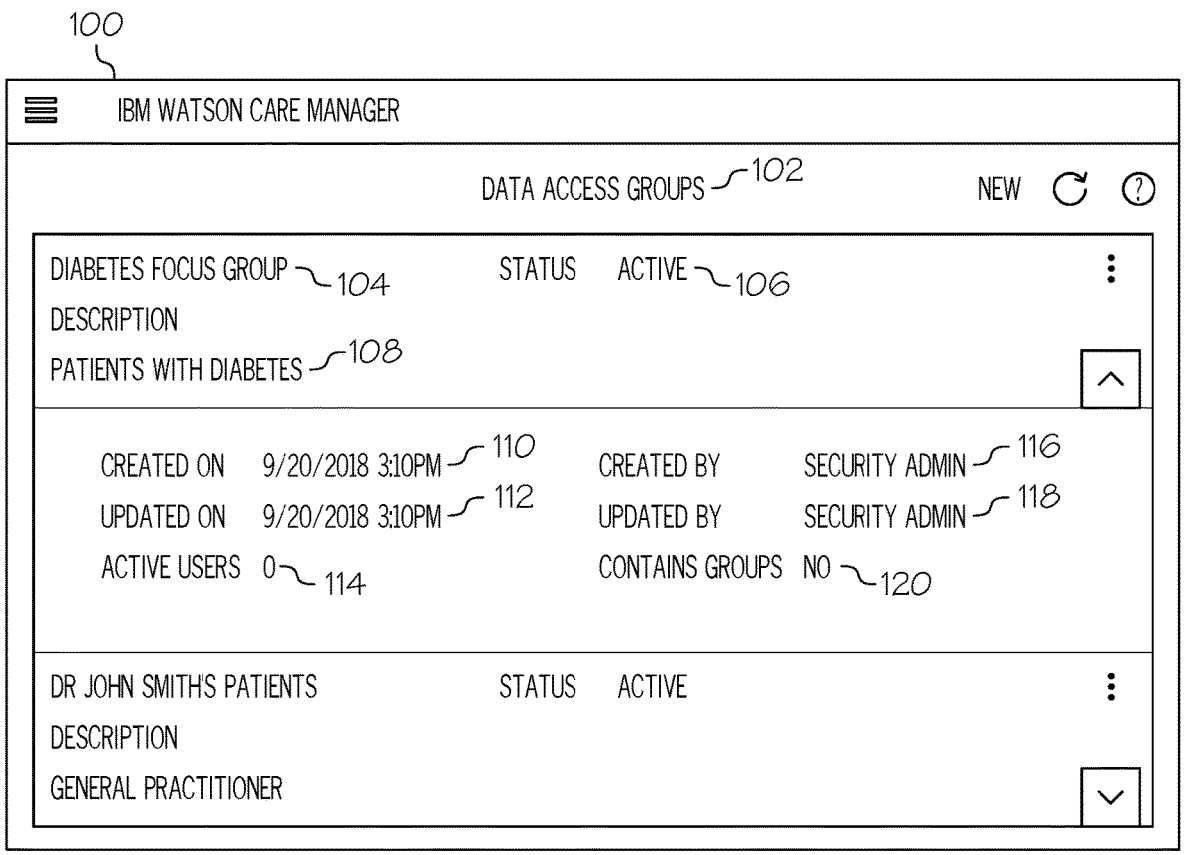
FIG. 1 is a screen of IBM Watson Care Manager illustrating data access groups.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting but merely as a basis for the claims and as a representative basis for teaching one skilled in the art to variously employ the present invention in virtually any appropriately detailed structure. Further, the terms and phrases used herein are not intended to be limiting; but rather to provide an understandable description of the invention.

Access groups for granting access to data is well known. In contrast, the inventor of this invention has designed and implemented a unique and novel data access group authorization engine. Unlike previous use of access groups, the data access group authorization engine has the following characteristics:

Association of group users to individual patients;

Patient inclusion via association to other users, for example, care team of that patient;

Patient inclusion via complex stored data, for example, ConditionName=Diabetes;

Patient inclusion via subgroups, by facilitating a hierarchy of groups with patients;

Support for organization configuration of the above concepts; and

Authorization engine algorithm, which performantly and accurately determines user access to patients via groups, as custom defined by the organization.

The present invention provides to a user of a group access to all patients within that group. Each group can have one or more criteria, which add patients to that group based on the conditions of that criteria. The criteria types can be mixed within the same group, e.g. multiple care team criteria alongside dynamic data criteria. Patients can also be explicitly included or excluded from a group. Patients can qualify for many groups. Users can be members of many groups.

Although the use case described is specific to medical data, the extensible solution that can be used in any other application and will be especially beneficial in cases where quick, efficient, web-based access needs to be addressed. Stated differently, the present invention is applicable to other access data types other than patient's PHI, such as insurance data, banking and financial data, and other situations where a unique property of a person is used to grant access to other users.

Non-Limiting Definitions

The terms "a", "an" and "the" preceding an element or component are intended to include the plural forms as well, unless the context clearly indicates otherwise.

"Cache" is hardware or software component that stores data so that future requests for that data can be served faster than accessing a database file.

"Criteria" is one more attributes to be a member of a defined group. For example, in a criteria for diabetes there could be different criteria for different types of diabetes, e.g. type I and type II.

"Dynamic data" is patient or person data that has a temporal aspect to it or may change over time. Dynamic data includes clinical data, personal information data or a combination of both which is changes over time denotes the group membership of the person. Some examples of dynamic data include addresses, recorded vital readings such as blood pressure, and present or past illnesses. Each attribute and value has a relevant time period as to represent current applicability while also facilitating a "patient's history. When dynamic data is active for a patient in the current time period, the data qualifies for use with Access Group Criteria. When dynamic data changes, this also affects the configured Access Group Criteria. For example, if the Diabetes condition is removed from a patient, the patient will no longer qualify for a Criteria that is defined with the Diabetes condition.

"Group" as used in computing, refers to a grouping of users. The users may belong to none, one, or many groups (although in practice, some systems place limits on this.) The primary purpose of user groups is to simplify access control to computer systems.

"Guice" is an open-source software framework for Java released by Google. It provides support for dependency injection using annotations to configure Java objects. Dependency injection is a design pattern whose core principle is to separate behavior from dependency resolution.

"IBM Watson Care Manager" or "WCM" is a cloud-based care management solution to help your organization to focus on individual-centered care. Care teams can capture and assess structured and unstructured information, select targeted programs, and create individualized care plans. IBM Watson Care Manager helps to individualize patient care needs and recommend action on the optimal combination of treatment, services, and benefits adjusted to address changing biological, psychological, social, and functional needs.

"Person" is used interchangeably with "client", "patient" or anyone else in which a user is seeking access to a person's information, such as personal health information, financial information, banking information, investing information, criminal record information, and more.

"Roles" as used in computing, refers to a set of permissions that are assigned to an entity, such as a hospital or care manager, so they can perform tasks that users would not normally be allowed to do.

"User" is used interchangeably with "doctor", "administrator", "health professional", "care team" and any other user of the WCM system that requests access to a person's information.

User Types and Descriptions

The following table is a descript of the different user types and their description used with the IBM Watson Care Manager.

| Users | Description |
|---|---|
| Standard users | Members of your organization who use Watson Care Manager applications only. Watson Care Manager manages the ' 'user's authentication and password reset process. Standard users receive an email with instructions to complete their sign-up and set their password. They sign in with their username and password from the Watson Care Manager sign in page. They cannot use the same details to sign in to other IBM Watson Health applications. |
| Single sign-on (SSO) users | Members of your organization who use Watson Care Manager applications and other systems by signing in with a single username and password. Single sign-on users sign in to Watson Care Manager applications by clicking the Single Sign-On link on the sign in page. You ' 'organization's identity provider authenticates the """"""" 'user's details when user signs in to Watson Care Manager, and manages their username and password reset process. |
| Reporting users | Members of your organization who use the Reporting application. Reporting users are standard users with access to reporting. A security administrator gives the users access by assigning an appropriate reporting role to each user in the Reporting application. |
| IBM Watson Care Manager Connect Individuals users | Clients who use the IBM Watson Care Manager Connect Individuals application. Clients are invited by care team members to register with the application. They receive an email with instructions to complete their sign-up and set their password. |
| IBM Watson Care Manager Connect Providers users | Community service providers who use the IBM Watson Care Manager Connect Providers Connect. Service providers are invited by administrators to register with the application. They receive an email with instructions to complete their sign-up and set their password. |

Example Administrator Screens

Turning now to FIG. 1 is a screen 100 of IBM Watson Care Manager illustrating data access groups. Any number of groups may be created. In this example, the data access group 102 is shown for a Diabetes Focus Group 104. The description of this group is patients with diabetes 108. The status of this access group is "active" 106. The status could also be set to "inactive". Auditing data is useful for the Health Insurance Portability and Accountability Act of 1996 (HIPAA) or any other compliance, such as, when the data access group was created 110, when the data access group was updated, how many active users 114, who created the data access group 116 and who updated the data access group 118. Lastly, show if the group is a hierarchical group 120 containing any other groups.

The IBM Watson Care Manager allows administrators to define custom data access groups, giving users access to patients based on certain "criteria". The criteria include: i) patients of a specific care team member, e.g., Dr. Smith's patients; ii) patients with certain dynamic data, e.g., a condition of asthma; iii) patients in another data access group (i.e., a subgroup); and explicitly including or excluding a person or patient from a data access group.

The present invention implements an authorization engine that examines the organization-defined custom data access groups to determine whether a care manager has access to that patient and all of their PHI.

Figure 2:
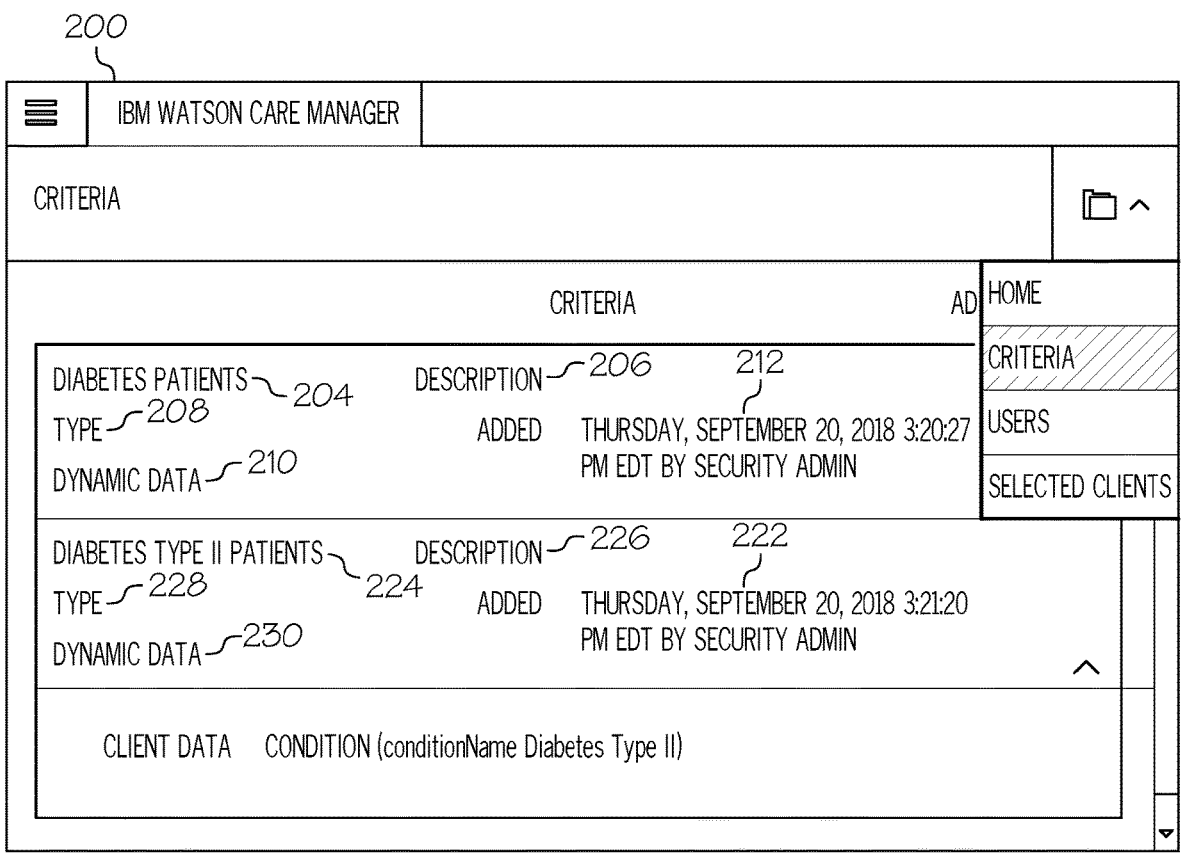
FIG. 2 is a screen of IBM Watson Care Manager illustrating criteria for data access groups of FIG. 1.

FIG. 2 is a screen of IBM Watson Care Manager illustrating criteria 202 for data access groups of FIG. 1 in which an administrator may interact. There are several different ways to define criteria for a data access group, and this is captured in FIG. 2 and FIG. 3. The first way to define criteria for a group is shown in FIG. 2. There are two criteria. There is one criterion for diabetes patients 204 and one criterion specifically for diabetes type II patients 224. Shown is diabetes patients 204 with a description 206 and type 208, when it was added 212 and client data 210. Also shown are diabetes patients 224 with a description 226 and type 228, when it was added 222 and client data 220. Type 228, as used here, is a type of criteria, e.g., Care Team data versus client data.

Figure 3:
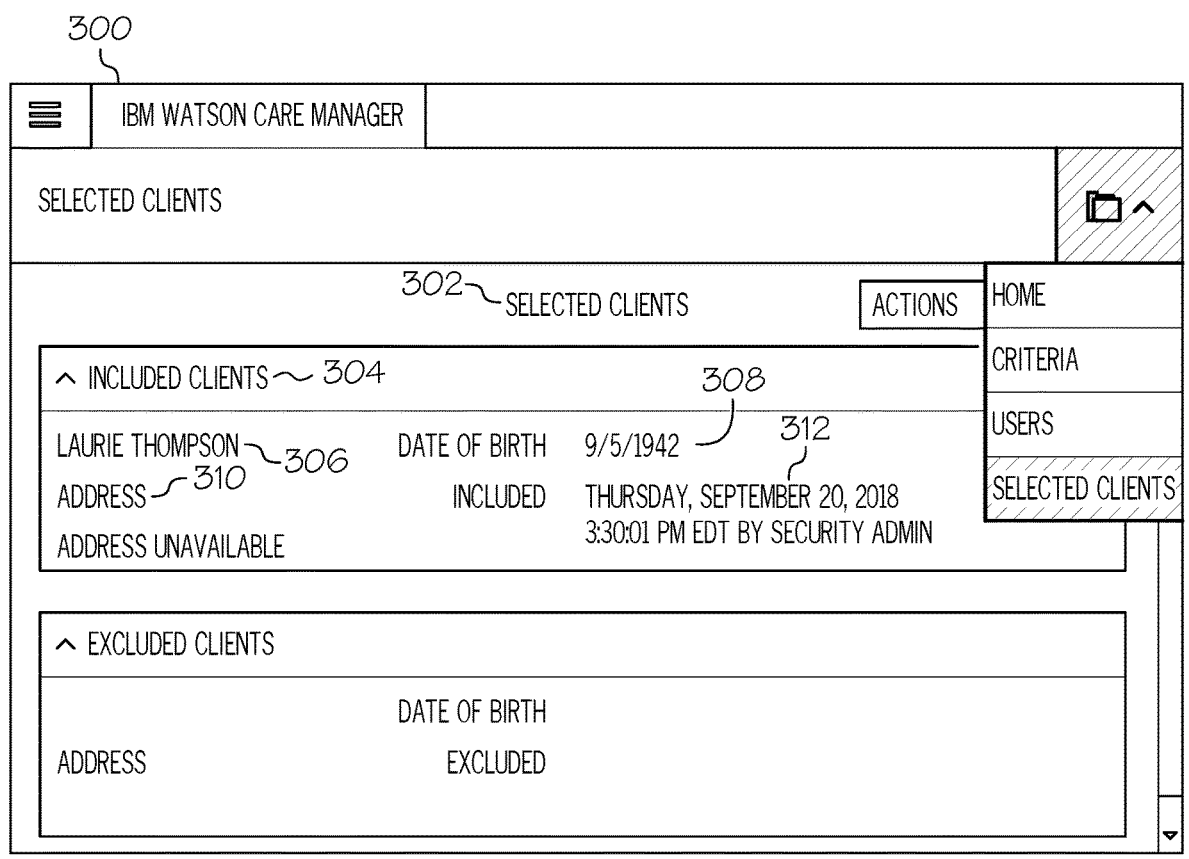
FIG. 3 is a screen of IBM Watson Care Manager illustrating included and excluded patients or persons from a data access group of FIG. 1.

FIG. 3 is a screen of IBM Watson Care Manager illustrating included and excluded patients, persons, or clients for data access groups of FIG. 1 in which an administrator may interact. Explicit inclusion and explicit inclusion is another way for an administrative user to define criteria for a data access group. This screen is an example to explicitly choose which patients are in the data access group and which patients are explicitly excluded. Shown for a selected client 302 is who should be included 304 and the details of the client e.g. name 306, date of birth 308, address (postal or residential) 310, and date entered in this included group. For example, if someone did not show all the early indications of diabetes but they are suspected to be in a pre-diabetes state, they can be explicitly added to the group. Likewise, not shown, there are screens that the administrator can interact with to explicitly exclude a user. For example, if there are twenty patients in a diabetes clinical study group based on the criteria. A patient may be explicitly excluded from the group even though they meet the criteria because the group size is too large and capped at a number less than twenty.

Hierarchical Groups

Figure 4:
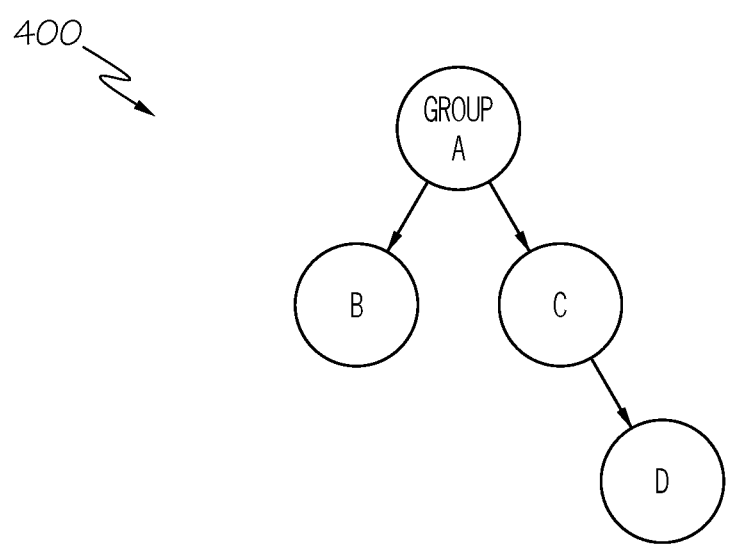
FIG. 4 is a hierarchical group.

FIG. 4 is a hierarchical group 400. Shown are four groups A, B, C, D. The hierarchy relationship is A is the group with B as a member. Also, C and D are members. This is a tree structure.

There are a few core ideas with the use of group hierarchies. To begin, when adding a subgroup to a parent group, all patients in that subgroup are added to the parent group. Users of the subgroup are not inherited, however. Subgroup definitions allow a group hierarchy to be defined. Stated differently, the criteria of all one sub-group can be a member of a higher-level group. Third, a group contains the set of its own patients plus the clients of its subgroups, i.e., subgroup patients are inherited by the parent. A={patients of A, B, C, D}. Users are explicitly added as members of one or more groups. Users can be members of more than one group in the same hierarchy; however, group users are not inherited. Group depth is limited to a maximum to reduce computational complexity. In one example, the maximum is 6, but other maximum numbers can be used as the cost of computer processing capabilities permits. Group hierarchies cannot be circular (for example, A→B→A).

Data Access Authorization Engine

Figure 5:
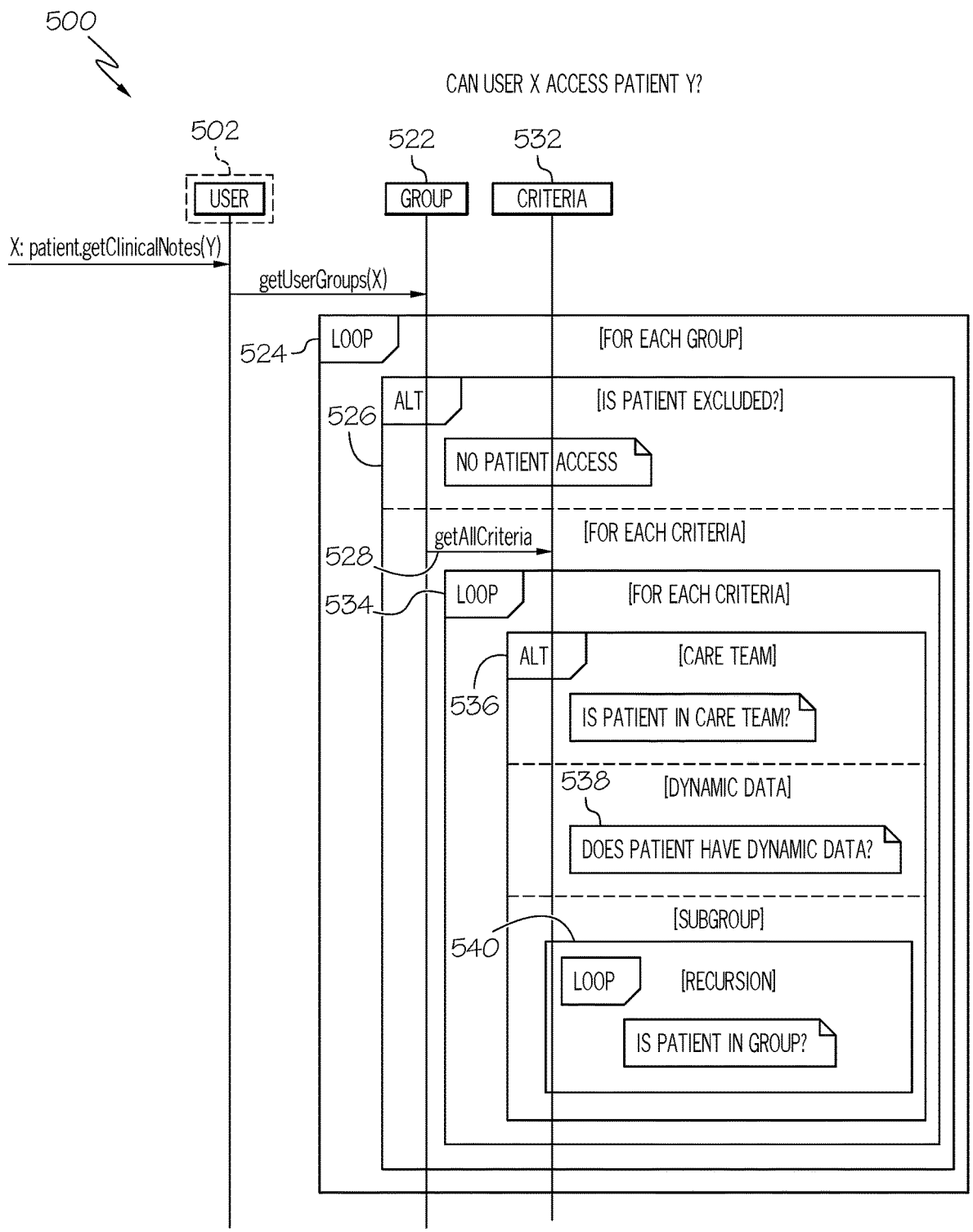
FIG. 5 is a diagram of a data access authorization engine handling a hierarchical group of FIG. 4 using iterative grouping.

Turning now to FIG. 5 is diagram 500 of a data access authorization engine handling a hierarchical group of FIG. 4 using iterative grouping. Beginning with an overview, this is where the data access authorization engine determines if a user request X can access patient Y information. When a user X attempts to access the PHI of patient Y, the request is intercepted and redirected to the Data Access Group authorization engine. This is achieved via AOP API interception techniques using Guice. Other software method interception techniques can be used with or without the JAVA programming environment. The data access group authorization engine is then responsible for allowing or rejecting the request. The decision is made based on the organization-defined Data Access Groups, and subsequently, the engine algorithm. The data access group authorization engine works on an inclusion principle "if the user is a member of a group, and the group contains that patient, stop processing and allow the request." Stated differently in diagram 500, once any test is completed that denotes being included or excluded in a group membership, the processing stops without executing any other test. This is the fastest approach possible. Intelligent caching of all group structures and patient-group membership makes this even faster, as further discussed below.

For example, conventional group access engines require parsing complex data structures to determine if the patient is a member of a data access group anytime a user tries to access a patient's PHI. Further, each condition of the patient must be individually checked. Returning to the diabetes example, the conventional group access engine executes queries to determine whether the patient has diabetes. The other check is to determine if the current user is a member of the group. This patient-side test and the user check is a computationally expensive check, especially if this check is being repeated often by a user for a lot of different patients and for many patient data requests per patient.

The diagram illustrates a user request 502 being received to access data associated with a person from a file system or database. Shown is at least one software method patient-.getClinicalNotes( ). Because this method matches a defined method for the interception, this method is intercepted by performing method interception.

The method getUserGroups(X) is executed, in which X is the user X requesting access to patient Y's record. Next, at least one group membership 522 is accessed based on the user request 502 and at least one group membership of the person or patient. An outer loop 524 is entered for each group in the group hierarchy. A test is made 526 to determine if the patient Y's PHI information being requested by user X is explicitly included or excluded. If the patent Y's PHI information is explicitly included than patient Y's PHI information is returned to the user X and no further processing is needed. Likewise, if the patent Y's PHI information is explicitly excluded than patient Y's PHI information is not returned to the user X, and no further processing is needed.

Next, if no explicit inclusion or exclusions are made, the process continues to a second inner loop 534. For each criterion, a test is made getAllCriteria to determine if patient Y is qualified to be a member of the data access group. For example, is patient Y in the care team 536. If the criteria is a dynamic data 538 criteria, check if the patient has the specified dynamic data value to determine if the patient or person is a member of the data access group. The inner loop 534 is repeated for each criterion in the criteria being examined.

If the group is part of a hierarchy of groups, like that shown in FIG. 4, the process repeats iteratively for each subgroup in the hierarchy but for the group(s) in the hierarchy that have already been through the outer loop.

Figure 6:
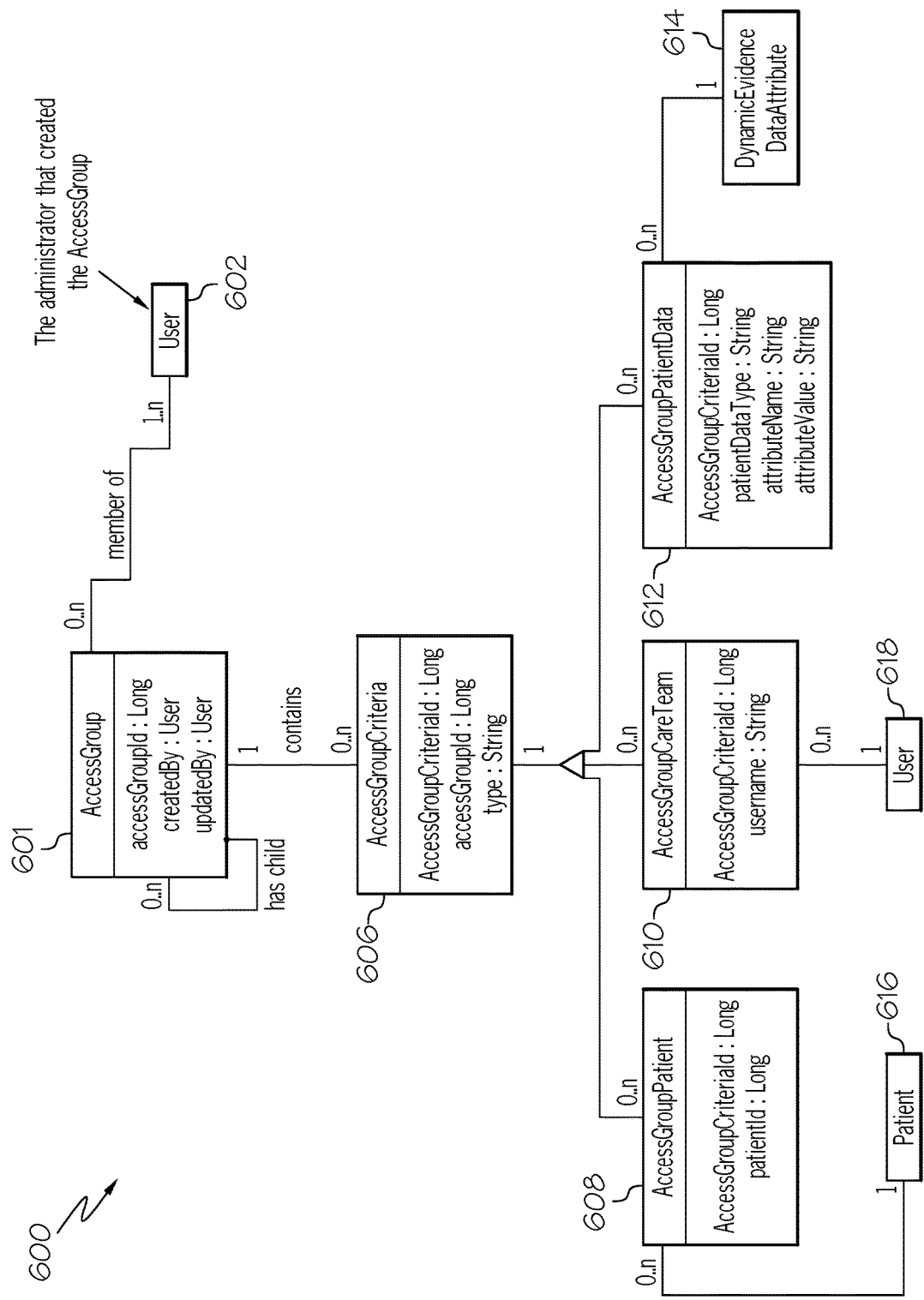
FIG. 6 is a schema used by the data access authorization engine of FIG. 5.

FIG. 6 is a schema 600 used by the data access authorization engine of FIG. 5. This is when an administrator defines a data access group and the criteria within the group. The administrator 602 creates this access group containing a set of users and criteria (each containing patients), to enable the user's access to those patient's data. 604. Each criteria has specific data applicable to that criteria, such as the patientId for the care team, or attribute names and values for dynamic data.

AccessGroupDef 606 is criteria or access group criteria.
AccessGroupClient 608 is definition for a patient or person for a data access group.
AccessGroupCareTeam 610 is criteria or user access to the data access group.
AccessGroupPatientData 612 is criteria based on patient data.
DynamicEvidenceDataAttribute 614 is dynamic data.
ConcernRole 616 is a patient or person.
User 618 is a non-administrator user or doctor that administrates the care team. For example, Dr. Smith may be linked to three persons on his care team.

Flow Diagram

Figure 7:
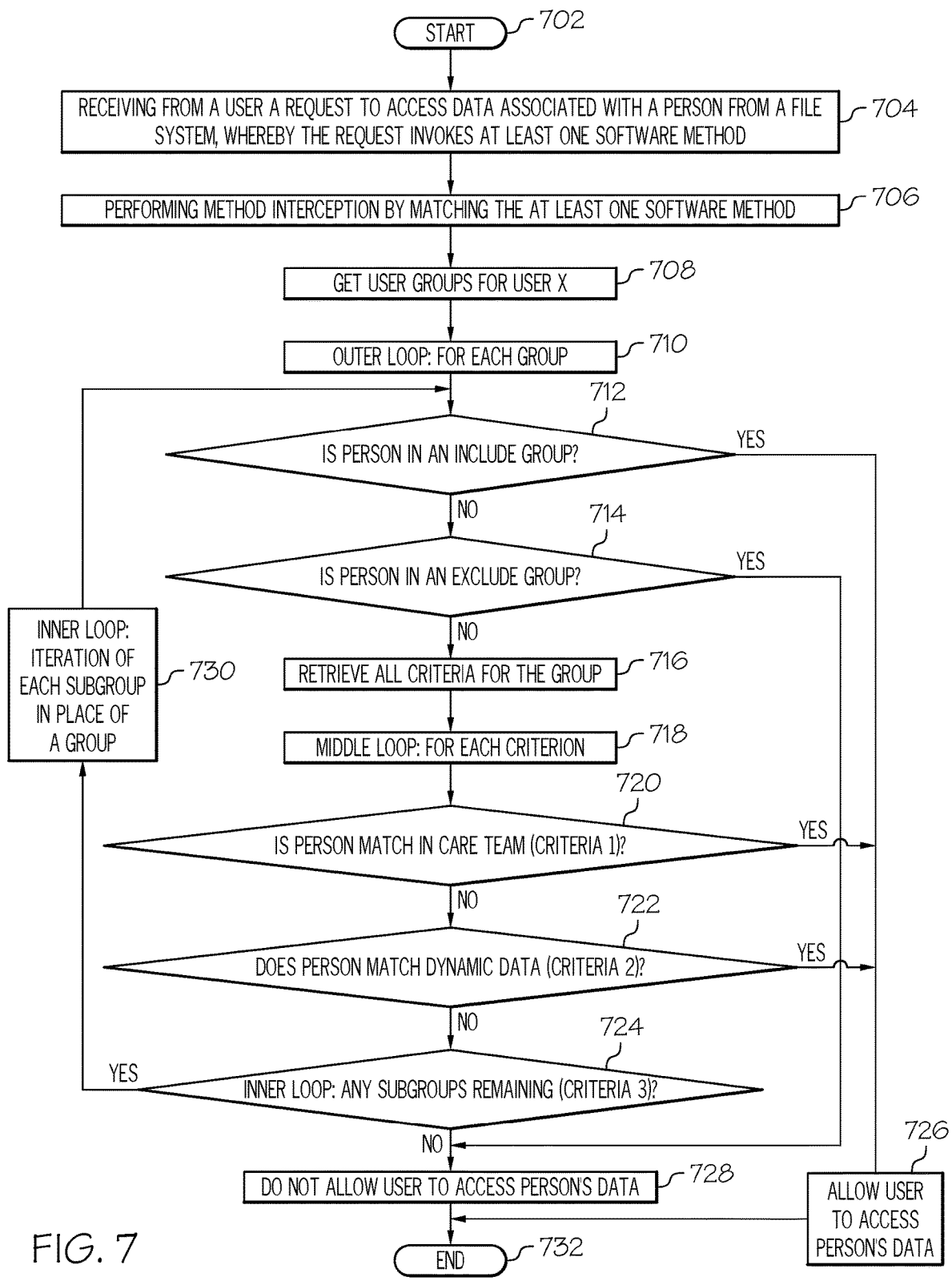
FIG. 7 is a flow diagram of the data access authorization engine processing a request from a user.

FIG. 7 is a flow diagram 700 of the data access authorization engine processing a request from a user. The process begins at step 702 and immediately proceeds to step 704. In step 704, a user requests access data associated with a person from a file system, whereby the request invokes at least one software method. The process proceeds to step 706. In step 706, method interception is performed by matching the at least one software method. The technique for method interception, such as via Aspect Oriented Programming (AOP) API interception techniques using Guice. The process continues to step 708. In step 708 the groups for user (X) are accessed. The process continues to step 710, which is an outer loop for each group as shown. The process continues to step 712.

In step 712 a test is made to see if the person (Y) is explicitly included in a group. If the result is "Yes," the process flows to step 726 in which the user (X) is granted access to person's (Y) data, and the process ends in step 732. Otherwise, if the result is "No," the process flows to step 714. In step 714, a test is made to determine if the person (Y) is explicitly excluded from the group. If the result is "Yes," the process flows to step 728, in which the user (X) is denied access to person's (Y) data, and the process ends at step 732. Otherwise, if the result is "No," the process flows to step 716. In step 716, all the criteria for the group is retrieved, and the process flows to step 718.

In step 718 a middle loop for each criterion of the criteria retrieved in step 716 is started as shown. The process continues to step 720, which is the first of a series of tests based on criteria. Step 720 a test is made to determine if the person is part of a care team (criteria 1). If the result is "Yes," the process flows to step 726, in which the user (X) is granted access to person's (Y) data, and the process ends in step 732. Otherwise, if the result is "No" the process flows to step 722. In step 722, a test is made to determine if the person is associated with the specified dynamic data (criteria 2). If the result is "Yes," the process flows to step 726, in which the user (X) is granted access to person's (Y) data and the process ends in step 732. Otherwise, if the result is "No," the process flows to step 724. In step 724, an inner loop is entered in which a determination is made if there are any sub-groups that are part of the group.

If the result is "No," the process flows to step 728, in which the user (X) is denied access to person's (Y) data and the process ends at step 732. Otherwise, if the result is "Yes," the process flows to step 730. In step 730, the inner loop is iterated by examining each subgroup in place of the group, and the process returns to step 712.

Intelligent Caching

Performance is a key factor of the data access group authorization engine. Performance is particularly important when:
 There are high volumes of patient dynamic data.
 The organization defines complex group+subgroup structures. In one example, the hierarchy 5 levels deep but other levels of hierarchy are possible.
 The user requests a variety of different PHI across many different patients
 The question "does the user have access to this patient?" is asked on a highly frequent basis
 It is important to strike a balance between performance and accuracy
 Performance requires caching, which reduces accuracy (cached data on group structures or patient group membership leads to decisions on old information)
 Accuracy requires regular cache flushing, which reduces performance
 In general, we cache the structure of all groups, criteria, users and patient membership.

In general, most of these cache entries live for approximately 5 minutes (some live forever until flushed explicitly).

In general, the cache entries are flushed explicitly when group membership changes or patient data changes in a very specific way that would affect these groups.

Intelligent caching of all group structures and patient-group membership results in the data access group authorization engine performing even faster. For example, when the list of patients that has diabetes has changed, the underlying cache must be refreshed. So the cache can update when one or more of the following changes:
 the criteria denoting the at least one group membership,
 the group membership of the person,
 the group membership of the user,
 a hierarchical structure of the group and any subgroups, and
 temporal data, which is clinical data, personal information data or a combination of both Additional criteria types and examples of access groups include:
 The administrator can create groups based on the program types that the patient is assigned to. For example: Create a group for all patients in a specific clinical study.
 The administrator can create a rule that allows groups to be dynamically created. For example: Jim creates a new Group and selects "Dynamically by Data Type" as the Rule. Jim selects the Data Type "Court Appointment" and selects the attribute "county". When a new court appointment is created with a value of "County Meath" the system looks to see if there is already an existing Group with this Rule and the value of "county=Meath" if none exists then it will create a new Group for "county=Meath."
 Creates a group based on a set operation between two other groups. For example John selects the Group of all Patients with Asthma, he selects a Group of all Patients with Diabetes and he selects the Intersection operation to create a Group of all Patients with Diabetes and Asthma.

Where the care worker in WCM is also a user on an independent external or remote software system, if I can access patient X on the external system and that patient exists in WCM I can also access them in WCM. This enables alternative sources of information on group membership from external systems.

WCM can expose a service that allows external software systems to determine if a user has access to a patient. This enables external systems to perform their own software methods to accept or reject data access for the same user to PHI of the same effective patient.

The administrator can disable the ability of any administrator to create groups or enable the data access authorization engine. In effect, disable the engine and all its effects on user access to patient PHI.

When importing data from external systems, the administrator can configure to exclude the imported data from the use of analysis with the data access group authorization engine.

Administrators can add multiple users, criteria or patients to a group in a single operation.

Administrators can create a group with a rule that encompasses all patients (the Universe of Patients). For example: When logging into a test system, user X has been assigned to the Universe Group. This user can then access all patient data on the system.

Reporting and Logging

As part of the applying access groups for controlling data access, the present invention includes logging automatically as part of the data access authorization engine. Logging each user requesting access to each patient's PHI will help with logging compliance, including compliance with the Health Insurance Portability and Accountability Act of 1996 (HIPAA). The logging includes the response to the conditions being verified in a database, wherein the logging includes the user request, the group membership of the user, the person, the group membership of the person, and a result of whether the conditions were verified.

Operating Environment

Figure 8:
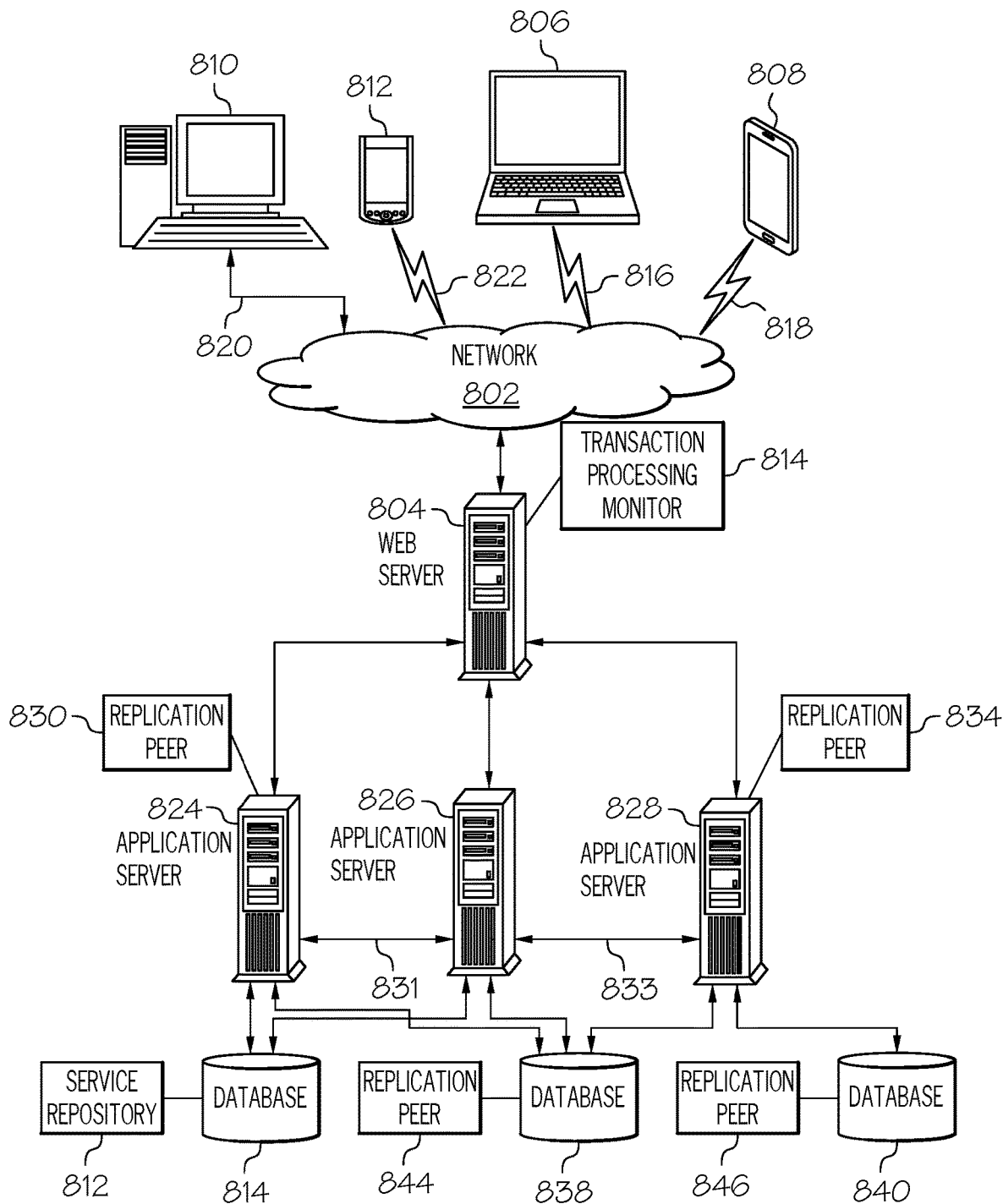
FIG. 8 is the n-tier architecture upon which diagrams of FIG. 1 through FIG. 7 can operate.

FIG. 8 is the n-tier architecture upon which diagrams of FIG. 1 through FIG. 7 can operate. It should be noted that although the following discussion is directed to a cloud computing environment, various embodiments are not limited to such environment and are applied to non-cloud computing environments as well.

It is important to note that although only a 3-tier architecture is shown, those of average skill in the computing arts will appreciate that this architecture can be easily extended to four or more tiers as in a multi-tier or n-tier system.

Referring to FIG. 8, shown is a multi-tier system architecture with a tier of clients 810, 812, 806, 808, a tier of application servers 824, 826, 828, and a tier of non-volatile storage in databases 838, 840. This multi-tier client/server architecture improves performance and flexibility for systems with a large number of users. Flexibility in partitioning can be as simple as "dragging and dropping" application code modules onto different computers in some multi-tier architectures.

This multi-tiered system has evolved from a more conventional system architecture in which clients retrieve information from a database, process the data according to instructions from a user, and store the data in the database. The clients in the conventional system architecture have three types of computer instructions installed and running on them to process information: code for the user interface (displaying buttons and lists of data), code for interacting with the database to fetch or store data, and code that processes the fetched data according to commands from the user interface or business logic. In contrast, in the multi-tiered system architecture, the client may contain only user interface code. The code for interacting with the database and processing the data is installed and operating on a middle-tier of servers such as application servers of FIG. 8. The middle tier of servers interacts with the database and processes data on behalf of the client. The multi-tiered system of architecture, therefore, has these advantages: the forced separation of user interface and business logic, a low bandwidth requirement for the network, and the concentration of business logic code in a few machines—rather than inserting business logic into all application software on all of the thousands or millions of clients.

There are a variety of ways of implementing this middle tier, such as transaction processing monitors, message servers, or application servers. The middle tier can perform queuing, application execution, and database staging. For example, if the middle tier provides queuing, the client can deliver its request to the middle layer and disengage because the middle tier will access the data and return the answer to the client. In addition, the middle tier adds scheduling and prioritization for work in progress.

The exemplary web server 804 of FIG. 8 also has installed and operating on it a transaction processing monitor (TPM) 814. The TP monitor technology is a type of message queuing, transaction scheduling, and prioritization service where the client connects to the TP monitor (middle tier) instead of the database server. The transaction is accepted by the monitor, which queues it and then takes responsibility for managing it to completion, thus freeing up the client. The TPM 814 provides applications' services to many clients by multiplexing client transaction requests onto a controlled number of processing routines that support particular services.

The system of FIG. 8 includes several exemplary clients 810, 812, 806, and 808. A client is a computer or a process or thread running on a computer that requests resources or services from another computer. Exemplary clients of FIG. 8 include a personal computer 810 coupled to the network 802 through a wireline connection 820, a personal digital assistant (PDA) 812 coupled to the network 802 through a wireless connection 822, a laptop computer 806 coupled to the network 802 through a wireless connection 816, and a mobile telephone 808 which is coupled to the network 802 through a wireless connection 818.

The system of FIG. 8 includes a data communications network 802 which provides for data communications among clients 810, 812, 806, 808, and web server 804. A network is a group of computers coupled for data communications according to data communications protocols through other computers typically referred to as routers, bridges, or switches. (The routers, bridges, and switches are not shown on FIG. 8.

The system of FIG. 8 includes web server 804. A server is a computer or a process or thread running on a computer that receives, processes, and responds to requests for resources or services from another computer. A web server is a server that carries out data communication according to a hyperlinking protocol. A common example of a hyperlinking protocol is the HyperText Transfer Protocol, the foundation of the World Wide Web. The term 'web server' is used in this specification more broadly, however, to refer to any server that supports any hyperlinking protocol, including, for example, the Wireless Access Protocol (WAP), the Handheld Device Transport Protocol (HDTP), and others as will occur to those of skill in the art. The web server 804 provides static web pages in responses to clients as well as dynamic web pages in such formats as Java Server Pages (JSP), PHP Hypertext Processor (PHP) pages, Microsoft's Active Server Pages (ASP), and Common Gateway Interface (CGI) scripts, and others as will occur to those of skill in the art.

Some caution is advised in use of the terms 'client' and 'server' because whether a particular computer acts as a client or a server depends upon role. In the system of FIG. 8, for example, when web server 814 receives from personal computer 810 a request for a web page, web server 804 is acting as a server; when, however, web server 804 requests resources from application server 824 in order to fulfill the request from personal computer 810, web server 804 acts as a client.

The system of FIG. 8 also includes application servers 824, 826, 828 coupled for data communications to web server 804. The application servers 824, 826, 828 are also connected to databases 838, 840 and to each other 89, 833. The system of FIG. 8 also includes non-volatile storage in the form of databases 838, 840. The application servers 824, 826, 828 and the databases 838, 840 have installed and operating on them replication peers 830, 834, 844, 846. A peer is a computer or a process or thread running on a computer that has the same capabilities of requesting and responding to requests as other computers similarly situated in a network. A replication peer is a software module that stores on a replication medium sessions flushed from a replication queue. A replication peer 844, 846 may store a session from an application server 824, 826, 828 to non-volatile storage in a database 838, 840. A replication peer 830, 834 also may store 89, 833 a session from an application server 824, 826, 828 into remote random-access memory on another application server.

The arrangement of servers and other devices making up the exemplary system illustrated in FIG. 8 are for explanation, not for limitation. Data processing systems useful according to various embodiments of the present invention may include additional servers, routers, other devices, and peer-to-peer architectures, not shown in FIG. 8, as will occur to those of skill in the art. Networks in such data processing systems may be implemented as local area networks (LANs), wide area networks (WANs), intranets, internets, and others as will occur to those of skill in the art. Networks in such data processing systems may support many data communications protocols, including, for example, the Transmission Control Protocol (TCP), the Internet Protocol (IP), the HyperText Transfer Protocol (HTTP), the Wireless Access Protocol (WAP), the Handheld Device Transport Protocol (HDTP), and others as will occur to those of skill in the art. Various embodiments of the present invention may be implemented on a variety of hardware platforms in addition to those illustrated in FIG. 8.

Example System/Server

Figure 9:
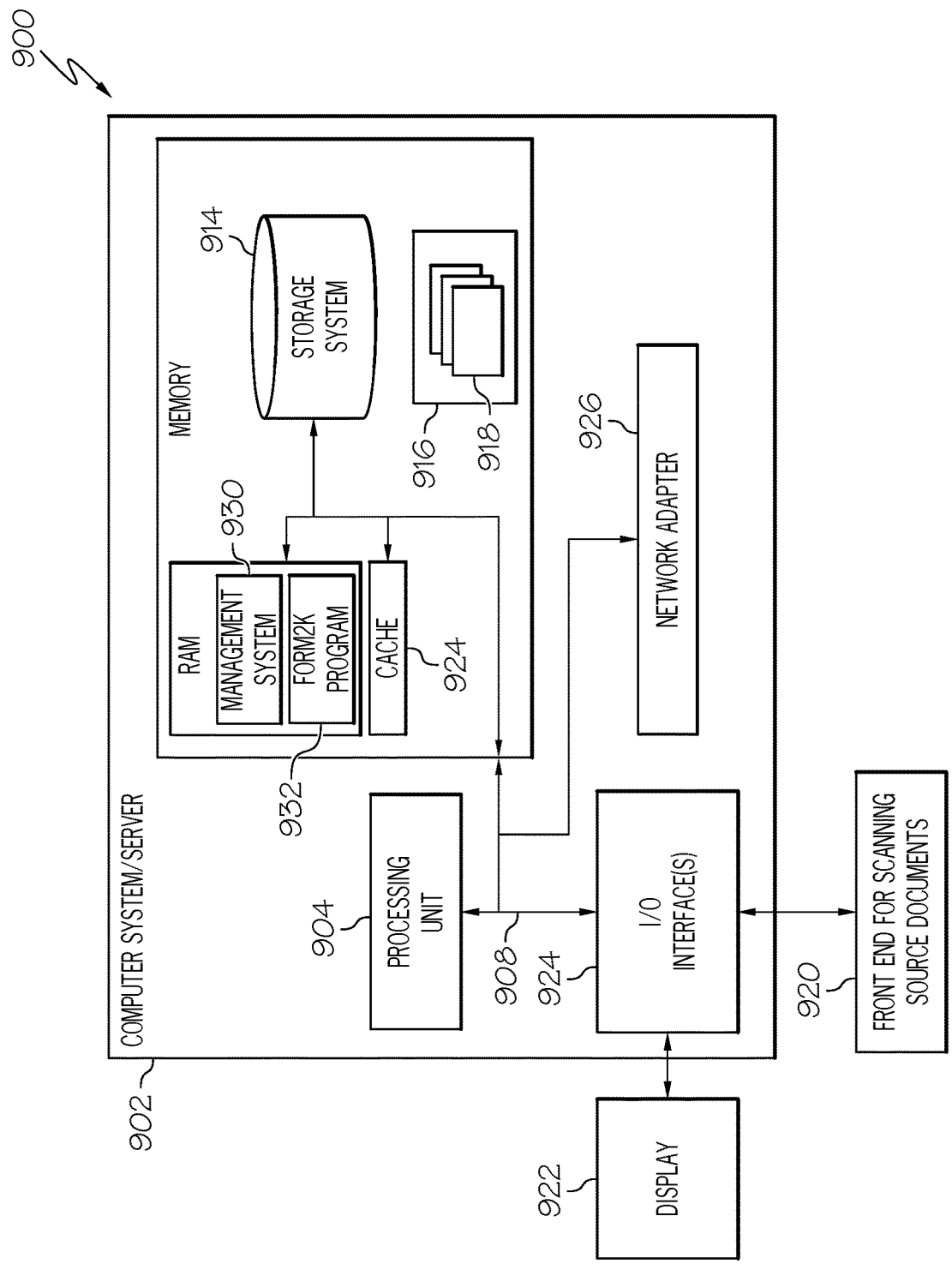
FIG. 9 is a block diagram of a computer system useful for implementing the software steps of the present invention.

FIG. 9 is a block diagram of a computer system useful for implementing the software steps of the present invention upon which diagrams of FIG. 1 through FIG. 7 can operate. FIG. 9 illustrates one example of a processing node and is not intended to suggest any limitation as to the scope of use or functionality of embodiments of the invention described herein. Regardless, the computing node 900 is capable of being implemented and/or performing any of the functionality set forth hereinabove.

Referring now to FIG. 9, this figure is a block diagram 900 illustrating an information processing system that can be utilized in embodiments of the present invention. The components of the information processing system 902 can include but are not limited to, one or more processors or processing units 904, a system memory 906, and a bus 908 that couples various system components, including the system memory 906 to the processor 904. The system memory 906 can include the computer code for FIG. 1 through FIG. 7.

The bus 908 represents one or more of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The information processing system 902 can further include other removable/non-removable, volatile/non-volatile computer system storage media. By way of example only, a storage system 914 can be provided for reading from and writing to a non-remov6able or removable, non-volatile media such as one or more solid-state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 908 by one or more data media interfaces. The memory 906 can include at least one program product having a set of program modules that are configured to carry out the functions of an embodiment of the present invention.

Program/utility 916, having a set of program modules 918, may be stored in memory 906 by way of example, and not limitation, as well as an operating system, one or more application programs, other program modules, and program data. Each of the operating system, one or more application programs, other program modules, and program data or some combination thereof, may include an implementation of a networking environment. Program modules 918 generally carry out the functions and/or methodologies of embodiments of the present invention.

The information processing system 902 can also communicate with one or more external devices 920 such as a keyboard, a pointing device, a display 922, etc.; one or more devices that enable a user to interact with the information processing system 902; and/or any devices (e.g., network card, modem, etc.) that enable computer system/server 902 to communicate with one or more other computing devices. Such communication can occur via I/O interfaces 924. Still yet, the information processing system 902 can communicate with one or more networks such as a local area network (LAN), a general wide area network (WAN), and/or a public network (e.g., the Internet) via network adapter 926. As depicted, the network adapter 926 communicates with the other components of information processing system 902 via bus 908. Other hardware and/or software components can also be used in conjunction with the information processing system 902. Examples include but are not limited to: microcode, device drivers, redundant processing units, external disk drive arrays, RAID systems, tape drives, and data archival storage systems. The external devices in one example include printers, scanners and imagers.

Non-Limiting Examples

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

The description of the present application has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

What is claimed is:

1. A method for applying access groups for controlling data access with intelligent caching, by a processor device, comprising:
   a) storing in a cache, at least one criteria denoting group membership, group membership of a person, group membership of a user, hierarchical structure of a group, hierarchical structure of any subgroups, and any temporal data;
   b) receiving from the user, a request to access requested data associated with the person from a file system, whereby the request invokes at least one software method;
   c) performing a method interception by matching the at least one software method;
   d) accessing at least one group membership of the user and at least one group membership of the person;
   e) determining whether two conditions are both verified i) the user is a member of a specific group and ii) the specific group contains the person;
   f) in response to the two conditions both being verified, then sending the requested data to a user device to display to the user;
   g) in response to the two conditions both being unverified, then denying access to the requested data; and
   h) updating the cache in response to one or more changes of the criteria denoting the at least one group membership, the group membership of the person, the group membership of the user, the hierarchical structure of the group, the hierarchical structure of any subgroups, and any temporal data.

2. The method of claim 1, wherein after accessing the at least one group membership of the person, includes a settable variable denoting if the person is excluded from the group membership of the person; and
   denying access to the requested data.

3. The method of claim 1, wherein after accessing membership of the person, includes a settable variable denoting if the person is included from the group membership of the person; and
   wherein in response to determining if each of the following conditions i) the user is a member of a specific group and ii) the specific group contains the person is verified is based on the settable variable.

4. The method of claim 1, wherein after accessing the group membership of the person includes determining if one or more criteria denotes the at least one group membership of the person.

5. The method of claim 4, wherein after accessing the group of the person includes determining if at least one or more criteria denotes the at least one group membership of the person further comprising:
   i) in response to the conditions not being verified, then determining if the at least one group membership includes more than one criterion in the one or more criteria; and
   j) in response to determining there is more than one or more criterion, then iteratively repeating each of steps c through j using the criterion in place of a criterion that was previously used in the group membership of the person.

6. The method of claim 4, wherein after accessing the group membership of the person includes determining if the person is associated with at least patient care team to denote group membership of the person, in which the patient care team is separate from the criteria used to denote membership.

7. The method of claim 4, wherein after accessing the group membership of the person includes determining if any temporal data which is clinical data, personal information data or a combination of both, changes over time denotes the at least one group membership of the person, in which the temporal data is separate from the criteria used to denote membership.

8. The method of claim 1, further comprising:
   i) in response to the conditions not being verified, then determining if the at least one group membership includes at least one subgroup membership; and
   j) in response to the at least one group membership including the at least one subgroup membership, then recursively repeating each of steps c through j using the subgroup membership in place of the group membership of the person.

9. The method of claim 1, wherein the performing the method interception by matching the at least one software method is part of an aspect-oriented programming implementation.

10. The method of claim 4, wherein the accessing the group membership of the person and the group membership of
   the user includes accessing at least one of the one or more criteria denoting the at least on group membership,
   the at least one group membership of the person, the at least one group membership of the user,
   the hierarchical structure of the group,
   the hierarchical structure of any subgroups, and
   temporal data, which is clinical data, personal information data or a combination of both from cache memory rather than the file system.

11. The method of claim 1, further comprising:
   i) logging the response to the conditions being verified in a database, wherein the logging includes the request from the user, the group membership of the user, the person, the at least one group membership of the person, and a result of whether of the conditions were verified.

12. A non-transitory computer program product tangibly embodying computer readable instructions which, when implemented, cause a computer to carry out the steps of a method for applying access groups for controlling data access with intelligent caching, comprising:
  a) storing in a cache, at least one criteria denoting group membership, group membership of a person, group membership of a user, hierarchical structure of a group, hierarchical structure of any subgroups, and any temporal data;
  b) receiving from the user, a request to access requested data associated with the person from a file system, whereby the request invokes at least one software method;
  c) performing a method interception by matching the at least one software method;
  d) accessing at least one group membership of the user and at least one group membership of the person;
  e) determining whether two conditions are both verified i) the user is a member of a specific group and ii) the specific group contains the person;
  f) in response to the two conditions both being verified, then sending the requested data to a user device to display to the user;
  g) in response to the two conditions both being unverified, then denying access to the requested data; and
  h) updating the cache in response to one or more changes of the criteria denoting the at least one group membership, the group membership of the person, the group membership of the user, the hierarchical structure of the group, the hierarchical structure of any subgroups, and any temporal data.

13. The non-transitory computer program product of claim 12, wherein after accessing the at least one group membership of the person, includes a settable variable denoting if the person is excluded from the group membership of the person; and
  denying access to the requested data.

14. The non-transitory computer program product of claim 12, wherein after accessing membership of the person, includes a settable variable denoting if the person is included from the group membership of the person; and
  wherein in response to determining if each of the following conditions i) the user is a member of a specific group and ii) the specific group contains the person is verified is based on the settable variable.

15. The non-transitory computer program product of claim 12, wherein after accessing the group membership of the person includes determining if one or more criteria denotes the at least one group membership of the person.

16. The non-transitory computer program product of claim 15, wherein after accessing the group of the person includes determining if at least one or more criteria denotes the at least one group membership of the person further comprising:
  i) in response to the conditions not being verified, then determining if the at least one group membership includes more than one criterion in the one or more criteria; and
  j) in response to determining there is more than one or more criterion, then iteratively repeating each of steps c through j using the criterion in place of a criterion that was previously used in the group membership of the person.

17. The non-transitory computer program product of claim 15, wherein after accessing the group membership of the person includes determining if the person is associated with at least patient care team to denote group membership of the person, in which the patient care team is separate from the criteria used to denote membership.

18. The non-transitory computer program product of claim 15, wherein after accessing the group membership of the person includes determining if any temporal data which is clinical data, personal information data or a combination of both, changes over time denotes the at least one group membership of the person, in which the temporal data is separate from the criteria used to denote membership.

19. The non-transitory computer program product of claim 12, further comprising:
  i) in response to the conditions not being verified, then determining if the at least one group membership includes at least one subgroup membership; and
  j) in response to the at least one group membership including the at least one subgroup membership, then recursively repeating each of steps c through j using the subgroup membership in place of the group membership of the person.

20. The non-transitory computer program product of claim 12, wherein the performing the method interception by matching the at least one software method is part of an aspect-oriented programming implementation.

21. The non-transitory computer program product of claim 15, wherein the accessing the group membership of the person and the group membership of the user includes accessing at least one of
  the one or more criteria denoting the at least on group membership, the at least one group membership of the person,
  the at least one group membership of the user,
  the hierarchical structure of the group,
  the hierarchical structure of any subgroups, and
  temporal data, which is clinical data, personal information data or a combination of both from cache memory rather than the file system.

* * * * *